US00PP33798P2

(12) United States Plant Patent
Ceciliano

(10) Patent No.: US PP33,798 P2
(45) Date of Patent: Dec. 28, 2021

(54) *DRACAENA* PLANT NAMED 'BRONZE BAY'

(50) Latin Name: *Dracaena deremensis*
Varietal Denomination: BRONZE BAY

(71) Applicant: FLORICA FARMS, INC., Eustis, FL (US)

(72) Inventor: Julio Gamboa Ceciliano, Santa Ana (CR)

(73) Assignee: FLORICA FARMS, INC., Eustis, FL (US)

( * ) Notice: Subject to any disclaimer, the term of this patent is extended or adjusted under 35 U.S.C. 154(b) by 0 days.

(21) Appl. No.: 17/184,908

(22) Filed: Feb. 25, 2021

(51) Int. Cl.
*A01H 5/12* (2018.01)
*A01H 6/12* (2018.01)

(52) U.S. Cl.
USPC ..... Plt./383

(58) Field of Classification Search
USPC ..... Plt./383
CPC ... A01H 5/12; A01H 5/00; A01H 5/02; A01H 6/12
See application file for complete search history.

(56) References Cited

U.S. PATENT DOCUMENTS

PP13,739 P2 * 4/2003 Fell, Jr. ..... A01H 5/00 Plt./383

* cited by examiner

*Primary Examiner* — June Hwu
(74) *Attorney, Agent, or Firm* — Foley & Lardner LLP

(57) ABSTRACT

The new variety 'BRONZE BAY' is a cultivar of the *Dracaena deremensis* plants. It can reach 1.5 m length in a 21 cm diameter pot, with an average of approximately 30-35 leaves per plant. The arrangement of the leaves are base wrapped around the stem. Shows a bright light green colored foliage, with central yellow stripes.

3 Drawing Sheets

Latin name of the genus and species of the claimed plant: *Dracaena deremensis.*

Variety denomination: 'BRONZE BAY'.

BACKGROUND

The present invention relates to a new and distinct cultivar of *Dracaena* plant, botanically known as *Dracaena deremensis* of the family of Asparagaceae, hereinafter referred to by the cultivar name 'BRONZE BAY'.

*Dracaena* is a monocotyledonous and tropical foliage plant which can be produced as a single or multi-stemmed plant, used mainly as a house plant for interior use or outdoors in shades in zones 9 or 10 only.

The new *Dracaena* 'BRONZE BAY' originated from an induced mutation over the *Dracaena deremensis* var. 'LIMELIGHT' (U.S. Plant Pat. No. 12,793). The new *Dracaena* 'BRONZE BAY' was discovered and selected by the inventor, Julio Gamboa Ceciliano as a single sprouting within a controlled environment, in Baltimore, Matina, Limón province, Costa Rica.

'BRONZE BAY' was grown in tropical lowlands in Costa Rica with day lengths of 12 to 13 hours and ambient temperatures of 65 to 85 degrees Fahrenheit. The light levels in lux were 30 K and the level of relative humidity was 80%.

Asexual reproduction of the new *Dracaena* 'BRONZE BAY' by vegetative cuttings was first performed in 2008 in Baltimore, Matina, Limón province, and demonstrated that the combination of characteristics as herein disclosed for the new cultivar are firmly fixed and retained through successive generations of asexual reproduction. The new cultivar reproduces true to type.

SUMMARY

The following traits have been repeatedly observed and are determined to be unique characteristics of 'BRONZE BAY', which in combination distinguish this *Dracaena* as a new and distinct cultivar:

1. Light green colored foliage, and yellow color stripes in the center of the leaf.
2. Wide and lanceolate leaves, 42-45 cm long and supported in a rosette.
3. 52 cm-1.5 m plant height in a 21 cm diameter pot.
4. Erect Plant habit
5. Plants of the new *Dracaena* 'BRONZE BAY' differ from plants of the parental cultivar, *Dracaena deremensis* 'LIMELIGHT' (U.S. Plant Pat. No. 12,793) and the commercial cultivar *Dracaena deremensis* 'HAWAIIAN SUNSHINE' (U.S. Plant Pat. No. 13,739) in the characteristics described in Table 1.

TABLE 1

Comparison between 'BRONZE BAY', 'LIMELIGHT', and 'HAWAIIAN SUNSHINE'

| Characteristic | New Cultivar *Dracaena deremensis* 'BRONZE BAY' | Parent *Dracaena deremensis* 'LIMELIGHT' (U.S. Plant Pat. No. 12,793) | Most similar *Dracaena deremensis* 'HAWAIIAN SUNSHINE' (U.S. Plant Pat. No. 13,739) |
|---|---|---|---|
| Plant Vigor | Less vigorous | More vigorous | More vigorous |

TABLE 1-continued

Comparison between 'BRONZE BAY', 'LIMELIGHT', and 'HAWAIIAN SUNSHINE'

| Characteristic | New Cultivar *Dracaena deremensis* 'BRONZE BAY' | Parent *Dracaena deremensis* 'LIMELIGHT' (U.S. Plant Pat. No. 12,793) | Most similar *Dracaena deremensis* 'HAWAIIAN SUNSHINE' (U.S. Plant Pat. No. 13,739) |
|---|---|---|---|
| Color | Bright, light green colored foliage, with central yellow stripes | Bright, glossy, yellow-green foliage which darkens to light-green as it matures | Bright, glossy dark green foliage with light green central stripes |
| Shape | Lanceolate leaves on a rosette | Lanceolate and leaves on a rosette | Lanceolate and leaves on a rosette |
| Texture of leaves | Smooth and waxy | Smooth and waxy | Smooth and waxy |

Of the many commercial cultivars known to the present inventor, the most similar in comparison to the new *Dracaena deremensis* 'BRONZE BAY' is the commercial cultivar 'HAWAIIAN SUNSHINE' (U.S. Plant Pat. No. 13,739).

BRIEF DESCRIPTION OF THE DRAWINGS

The accompanying photographs illustrate the overall appearance of the new *Dracaena deremensis* cultivar 'BRONZE BAY' showing the colors as true as is reasonably possible with colored reproductions of this type. Colors in the photographs may differ slightly from the color value cited in the detailed botanical descriptions which accurately describe the color of 'BRONZE BAY'.

DETAILED BOTANICAL DESCRIPTION

Figure 1:
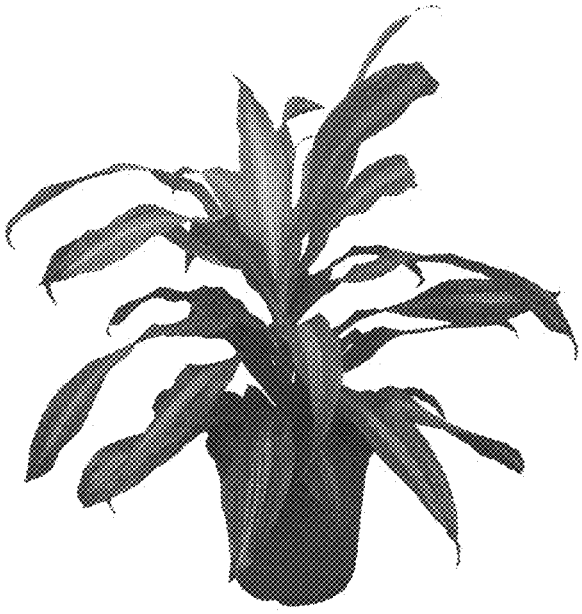
FIG. 1 shows a side view of a six-month old plant of *Dracaena* 'BRONZE BAY' in a 21 cm diameter pot.
Figure 2:
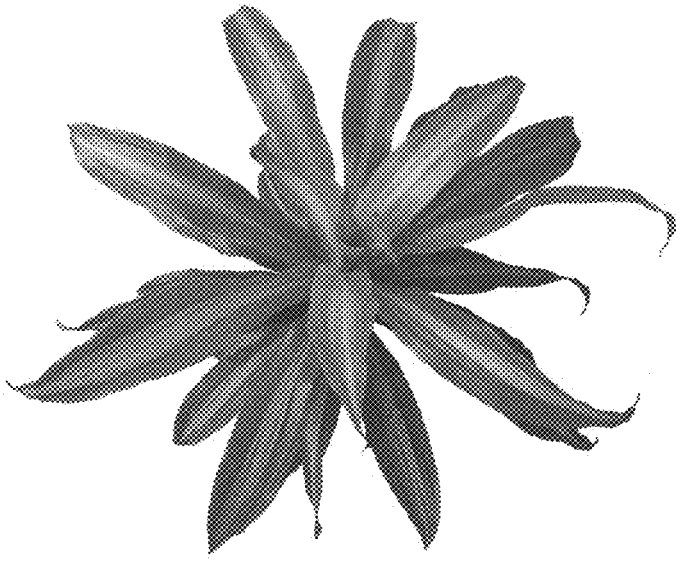
FIG. 2 shows a top view of a six-month old plant of *Dracaena* 'BRONZE BAY' in a 21 cm diameter pot.
Figure 3A:
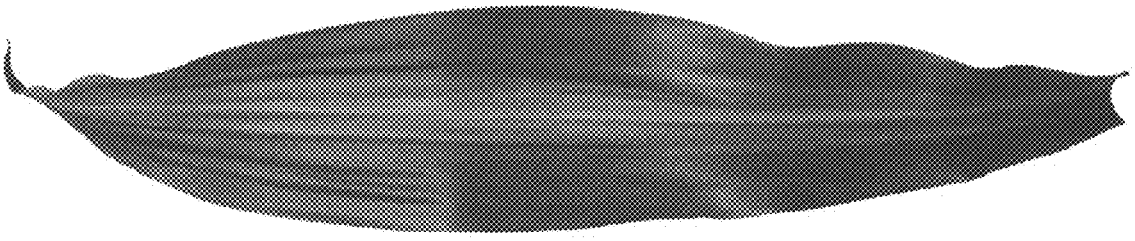
FIGS. 3A-3B show a close-up view of the typical leaves of *Dracaena* 'BRONZE BAY' from a six-month old plant (upper side 3A, under side 3B).
Figure 3B:
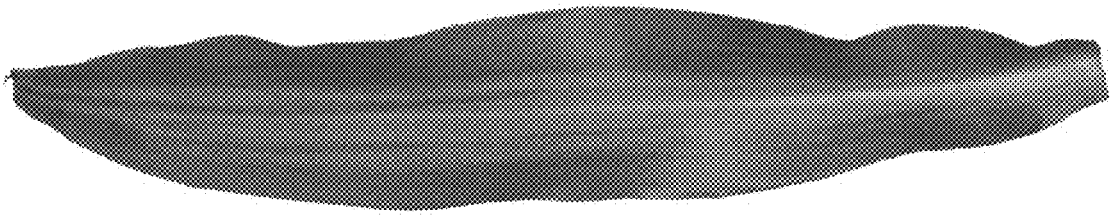

The new *Dracaena* 'BRONZE BAY' has not been observed under all possible environmental conditions. The phenotype of the new cultivar may show phenotypical changes with variations in environment such as temperature, light intensity, and day length without any change in the genotype of the plant.

The aforementioned photographs, together with the following observations, measurements and values describe the new *Dracaena* cultivar 'BRONZE BAY' as grown in open-field conditions at Baltimore, Matina, Limón province, Costa Rica, which closely approximate those generally used in commercial practice. Average temperature in Baltimore is 31° C. during the day and 24° C. at night. Plants grow under natural light conditions.

Plants of the new *Dracaena* cultivar 'BRONZE BAY' are grown under light conditions of about 80% shade from natural sunlight and about 80% relative humidity. No supplementary artificial light is necessary. Plants of the new *Dracaena* 'BRONZE BAY' are given 1) a liquid 24-8-16 fertilizer every 15 days, and 2) a granular Nutricote 18-6-12 fertilizer every 6 weeks in raining season. No growth retardants are used when growing plants of the new *Dracaena* 'BRONZE BAY'.

Color references were made according to The Royal Horticultural Society Colour Chart (R.H.S.) on line rhscf.orgfree.com. The photographs and descriptions were made during the dry season in Baltimore, Matina, Limón province, Costa Rica when outdoor day average temperature was 31° C. The age of the plants described is 8 months old.

Classification:

*Botanical.*—*Dracaena deremensis.*

*Variety denomination.*—'BRONZE BAY'.

Parentage: *Dracaena deremensis* 'LIMELIGHT' (U.S. Plant Pat. No. 12,793).

Optimal growth conditions:

*Light intensities.*—High adaptability to outdoor or indoor conditions.

*Temperature.*—Day: 18° C. to 28° C. Night: 14° C. to 22° C.

*Temperature tolerance.*—Tolerant to temperatures between 12° C. and 35° C.

*Fertilization.*—A liquid 24-8-16 fertilizer every 15 days, and a granular Nutricote 18-6-12 fertilizer every 6 weeks.

*Growth regulators.*—Not necessary.

Propagation:

*Type.*—Vegetative, by air layer or rooted cuttings.

*Rooting habit description.*—Easy to root. Roots are mostly fibrous and finely branched.

*Time to initiate roots.*—15 to 22 days at 20-25° C.

*Faster time to produce a rooted cutting.*—About 30 to 45 days at 20-25° C.

Plant:

*Growth rate.*—Approximately 77 cm annually.

*Form.*—Monocot; leaves whorled; leaf bases wrap around the stem.

*Plant height.*—Maximum of 4 m when grown in the ground and 1 m when grown in a container.

*Plant width.*—Single stem plant has an overall plant diameter of 56-76 cm wide.

*Stem-length.*—About 3.5 m when grown in ground; about 1 m when grown in 21 cm size container.

*Diameter.*—About 56-76 cm.

*Texture.*—Rough.

*Color.*—RHS N144C.

*Strength.*—Strong and durable.

*Internode length.*—About 20 mm to 40 mm.

Foliage:

*Quantity.*—About 30-35 leaves.

*Arrangement and attachment.*—Single, alternate; leaves whorled; leaf bases wrap around the stem.

*Leaf length.*—About 40-45 cm.

*Leaf width.*—About 6-8 cm.

*Overall shape of leaf.*—Lanceolated.

*Apex shape.*—Acute, triangular, and curved downwards.

*Base shape.*—Clasping to stem.

*Margin.*—Entire.

*Texture.*—Upper Surface: Smooth and waxy texture. Under Surface: Smooth and waxy texture.

*Pubescence.*—None.

*Color of mature leaf.*—Upper Surface: RHS N144C, and several RHS 3B complete and incomplete central stripes. Lower Surface: RHS N144C, and several RHS 3B complete and incomplete central stripe.

*Color of immature leaf.*—Upper Surface: RHS N144C, and several RHS 3B complete and incomplete central stripes. Lower Surface: RHS N144C, and several RHS 3B complete and incomplete central stripe.

*Central stripes average width.*—2.5-3 cm.

*Venation.*—Pattern: Longitudinal/parallel to the midrib Color.

*Leaf fragrance.*—None.

Inflorescence description: None observed.

Weather resistance: Drought tolerant.

Disease/pest resistance: None observed.

Disease/pest susceptibility: None observed.

I claim:

1. A new and distinct *Dracaena* plant named 'BRONZE BAY', as described and illustrated herein.

* * * * *